United States Patent [19]

Johnson et al.

[11] 4,355,162

[45] Oct. 19, 1982

[54] LAYERED COMPOUNDS OF MIXED OXIDES AND LEWIS BASES

[75] Inventors: Jack W. Johnson, Fanwood; Allan J. Jacobson, Princeton, both of N.J.

[73] Assignee: Exxon Research and Engineering Co., Florham Park, N.J.

[21] Appl. No.: 205,141

[22] Filed: Nov. 10, 1980

[51] Int. Cl.³ .................... C07F 11/00; C07F 13/00
[52] U.S. Cl. .................... 544/181; 544/225; 544/64; 546/2; 548/101
[58] Field of Search .................... 546/2, 10, 11, 12; 544/64, 225, 181; 548/101, 105, 109

[56] References Cited

U.S. PATENT DOCUMENTS

| | | | |
|---|---|---|---|
| 3,688,109 | 4/1972 | Gamble | 250/51.5 |
| 3,766,064 | 9/1973 | Gamble et al. | 252/25 |
| 3,980,684 | 9/1976 | Dines | 260/429 |
| 4,049,887 | 9/1977 | Whittingham | 429/112 |
| 4,094,893 | 6/1978 | Dines | 260/429 |

FOREIGN PATENT DOCUMENTS 1274594 9/1971 United Kingdom.
1377213 12/1974 United Kingdom.

OTHER PUBLICATIONS

Haner et al., Inorg. Chem. 1, 844, (1963).
Goldberg, Chem. Abs. 89, 43124y, (1978).
Khan, Chem. Abs. 71, 97880p, (1969).
Venien et al., Mat. Res. Bul. 14, 891–897, (1979).
Ladwig, Z., Naturforschung 20, 70–71, (1980).
Prasad et al., Indian J. Technology 15, 436, (1977).
Inglis, Chem. Abs. 75, 20202u, (1971).
Iovel #1, Chem. Abs. 85, 123034b, (1976).
Iovel #2, Chem. Abs. 87, 183719e, (1977).
Selbin et al., J. Inog. Nud. Chem. 24, pp. 1111–1119, (1962).
J. Bernard and M. Camelot, C. R. Acad. Sci., Paris, Ser. C, 263, 1068, (1966).
M. Camelot, Revue de Chimie Minerale, 6, 853, (1969).
G. Ladwig, Zeit. Anorg. Allg. Chem., 338, 266, (1965).
N. G. Chernorukov, N. P. Egorov and I. R. Mochalova, Russ. J. Inorg. Chem., 23, 1627, (1978).
N. G. Chernorukov, N. P. Egorov and V. F. Kutsepin, Russ. J. Inorg. Chem., 24, 987, (1979).

*Primary Examiner*—Mark L. Berch
*Attorney, Agent, or Firm*—James H. Takemoto

[57] ABSTRACT

A new composition of matter comprising the reaction product of a mixed oxide having layers of corner linked octahedra and tetrahedra and a Lewis base. The reaction product forms a layered compound of the formula $L_xMOM'O_4$ where $MOM'O_4$ is a mixed oxide selected from the group consisting of $VOPO_4$, $VOSO_4$, $VOAsO_4$, $VOMoO_4$, $NbOPO_4$, $NbOAsO_4$, $TaOPO_4$ and $MoOPO_4$, x is from about 0.1 to 1.0 and L is a Lewis base containing nitrogen or oxygen electron donor and is selected from the group consisting of 5-membered heterocyclic amines, 6-membered heterocyclic amines, amine oxides, triorganophosphates, phosphine oxides and sulfoxides. The layered compounds are characterized in that L is covalently bound to a metal atom in the $MOM'O_4$ layer.

9 Claims, 1 Drawing Figure

LAYERED COMPOUNDS OF MIXED OXIDES AND LEWIS BASES

BACKGROUND OF THE INVENTION

This invention relates to unique layered compounds formed by reacting mixed oxides with a Lewis base. More particularly, the Lewis base is covalently bound to a metal atom within a layered oxide structure.

It is known from U.S. Pat. No. 3,766,064 that heavy metal chalcogenides wherein the metal is titanium, vanadium, zirconium, niobium, hafnium, tantalum, palladium, platinum and gallium, and the chalcogenide is sulfur, selenium and tellurium can be intercalated with ammonia, hydrazine and organic nitrogen compounds. The general properties and methods of preparation are described therein. U.S. Pat. No. 3,688,109 relates to similar intercalated compounds useful as X-ray diffraction grating crystals. Intercalation compounds including molybdenum and tungsten with isonitrile and metallocene guests are disclosed in U.S. Pat. Nos. 4,094,893 and 3,980,684. U.S. Pat. No. 4,049,887 relates to an improved cathode containing as active material a layered compound of the formula $MA_xB_y$ where M is Fe, V, Ti, Cr or In, A is O, S, Se or Te and B is Cl, Br or I.

J. Bernard and M. Camelot, C. R. Acad. Sci., Paris, Ser. C., 263:1068 (1966) report on the reaction of molybdenum trioxide, molybdenyl chloride and molybdenum dioxydichloride with pyridine. In a subsequent work, M. Camelot, Revue de Chimie Minerale, 6, 853 (1969), studied addition compounds of pyridine with some oxychlorides or trioxides of chromium, molybdenum and uranium. Based on an infrared spectroscopic investigation, Camelot concluded that these compounds were molecular coordination compounds.

G. Ladwig (Z. Anorg. Allg. Chem., 338, 266 (1965)) relates to a structural study of $VPO_5 \cdot nH_2O$. It is reported on pages 273 and 274 that anhydrous $VPO_5$ takes up ammonia and amines with a one-dimensional lattice expansion to give a $VPO_5 \cdot 1.1NH_3$ reaction product. Pyridine was stated to show no lattice expansion. Hydrogen bonding was asserted to be important in determining the type of molecule that can react with $VPO_5$ layers. Similar structural studies involving niobium phosphate are reported by Chernorukov et al., Russian J. Inorg. Chem., 23, 1627 (1978); 24, 987 (1979).

SUMMARY OF THE INVENTION

It has been discovered that certain mixed oxides form new compounds having a unique layered structure. The composition of the invention comprises the reaction product of a mixed oxide having layers of corner linked octahedra and tetrahedra and a Lewis base, said reaction product forming a layered compound of the formula $L_xMOM'O_4$ where $MOM'O_4$ is a mixed oxide selected from the group consisting of $VPO_4$, $VSO_4$, $VOAsO_4$, $VOMoO_4$, $NbOPO_4$, $NbOAsO_4$, $TaOPO_4$ and $MoOPO_4$, x is from about 0.1 to 1 and L is a Lewis base containing nitrogen or oxygen electron donors and selected from the group consisting of 5-membered heterocyclic amines, 6-membered heterocyclic amines, amine oxides, triorganophosphates, phosphine oxides and sulfoxides, the layered compound being characterized in that L is covalently bound to a metal atom in the $MOM'O_4$ layer. When prepared in the presence of a proton source, the layered structure is partially protonated to form a compound of the formula $L_xH_yMOM'O_4$, L, x and $MOM'O_4$ being defined as above, H is hydrogen and y ranges from about 0.1 to about 0.5.

The present compositions contain a neutral Lewis base which is covalently bound to a metal (M) atom in the mixed oxide ($MOM'O_4$) layers. The bonding is therefore similar to that which might be expected from a typical coordination complex. They are not, however, coordination complexes because of the layered structure which remains even after reaction with Lewis base.

BRIEF DESCRIPTION OF THE DRAWING

The FIGURE is a schematic diagram of the bonding arrangement in (pyridine)$VOPO_4$.

DETAILED DESCRIPTION OF THE INVENTION

Figure 1:
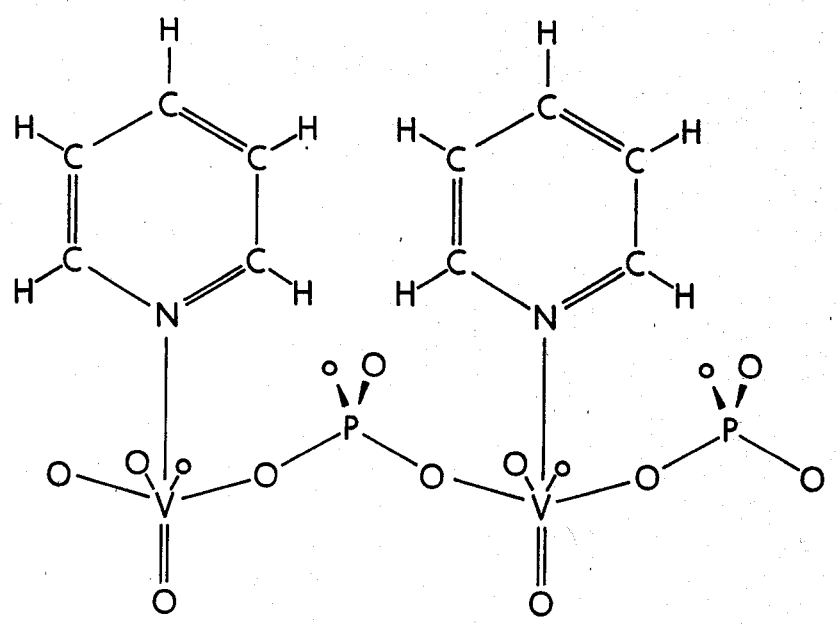

Lewis bases which form the layered compounds of the formula $L_xMOM'O_4$ are those which have heterocyclic nitrogen and oxygen donors, preferably 5- and 6-membered heterocyclic nitrogen donors, and x is preferably from about 0.4 to 1.0. Preferred nitrogen donors are pyridines having the formula

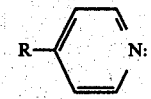

where R is hydrogen; halogen; $C_1$–$C_{20}$, preferably $C_1$–$C_{10}$ aliphatic; $C_6$–$C_{10}$ aryl, preferably phenyl which may be substituted by halogen or $C_1$–$C_6$ alkyl; $C_7$–$C_{20}$ aralkyl, preferably benzyl or phenylethyl; OR' or SR' where R' is $C_1$–$C_6$ alkyl. Examples are

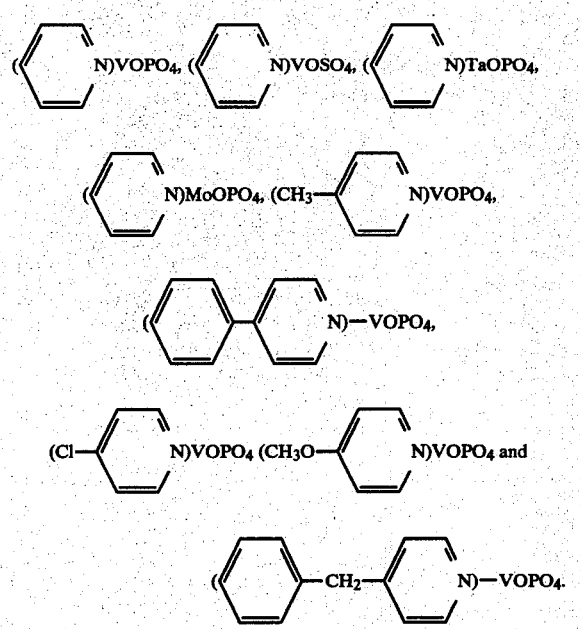

Other 5- and 6-membered heterocyclic amines which may form layered compounds include pyridazine, pyrimidine, pyrazine, triazine, N-substituted oxazine, N-substituted imidazole, oxazole, thiazole, 1,4-diazabicyclo[2,2,2]octane and

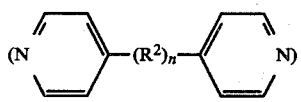

where n is 0 or 1 and $R^2$ is methylene; alkylene, alkene or alkyne of 2-6 carbon atoms; $C_6$-$C_{10}$ aryl, preferably paraphenylene, $C_7$-$C_{14}$ aralkylene; oxygen or sulfur. Oxygen donors may be amine oxides, triorganophosphates, phosphine oxides and sulfoxides.

Mixed oxides according to the invention are characterized in terms of layers of corner linked octahedra and tetrahedra, the layers being linked through the apical octahedron oxygens. The octahedra, however, are severely distorted with one very short and one very long metal-oxygen bond so that the resulting structure is actually layered rather than a three dimensional net. Mixed oxides may be hydrated, with the long metal-oxygen bond replaced by a coordinated water molecule. The layers in this instance are held together by hydrogen bonding. In the formula MOM'$O_4$, M is V, Nb, Ta or Mo and M' is P, As, S or Mo. Examples of mixed oxides which have the above-cited structural features are VOPO$_4$, VOSO$_4$ VOAsO$_4$, VOMoO$_4$, NbOPO$_4$, NbOAsO$_4$, TaOPO$_4$ and MoOPO$_4$. Preferred mixed oxides are VOSO$_4$, VOPO$_4$, VOAsO$_4$ and VOMoO$_4$, especially VOAsO$_4$ and VOPO$_4$.

If $L_x$MOM'$O_4$ is prepared in the presence of a proton source such as $H_2O$ or Bronsted acid, the layered structure is at least partially protonated to form a compound of the formula $L_xH_y$MOM'$O_4$ where L, x, MOM'$O_4$ are defined as hereinbefore, H is hydrogen y is from about 0.1 to about 0.5. While the precise structure is not known, protonation results in a change in the IR spectrum at about 1600 cm$^{-1}$, an enhanced esr signal and increased thermal stability.

The present mixed oxides of the formula MOM'$O_4$ are described in the literature, e.g., A. F. Wells, Structural Inorganic Chemistry, 4th ed., Oxford Press, London. Unlike the heavy metal chalcogenides employed in intercalation compounds such as those reported in U.S. Pat. No. 3,766,064, mixed oxides of the formula MOM'$O_4$ may be used without any special pretreatment. Thus, the mixed oxide is heated with an appropriate Lewis base in a sealed tube at temperatures of from 100° to 400° C., preferably 100° to 250° C. for up to about 21 days, preferably from about 1 to 7 days. The amount of Lewis base is not critical and a stoichiometric amount or an excess may be used. It is preferred to evacuate the tube prior to sealing to minimize the possibility of oxidation of Lewis bases at elevated temperature. At higher temperatures such as 250° C., it is possible that the mixed oxide itself can lead to oxidation of Lewis base. It also is preferred to use substantially anhydrous Lewis bases. An alternative preparation is to reflux the hydrated mixed oxide with either the Lewis base or the Lewis base dissolved in suitable organic solvent.

The layered compounds of the present invention do possess the covalent bonding characteristic of molecular coordination compounds. They are not, however, molecular coordination compounds since the layered structure of the mixed oxide is maintained even after reaction with Lewis base.

As noted previously, the octahedra in mixed oxides of the formula MOM'$O_4$ are very distorted with one very long and one very short metal oxygen bond. In the present invention, the very long metal oxygen bond is replaced by a strongly bound Lewis base which then produces a true layered compound by disrupting the weak interconnecting long metal oxygen bond. This is shown in the FIGURE, which is a schematic diagram illustrating the structure of (pyridine)VOPO$_4$. In order for the Lewis base to form a strong L-metal bond, it should not be sterically hindered, i.e., larger than the available space in the metal oxide structure. Thus, bulky Lewis bases such as tri-t-butyl amine and triphenylphosphine will not form layered compounds according to the invention.

When a bidentate Lewis base is incorporated into the LMOM'$O_4$ structure, it is possible that separate mixed oxide layers may be bound together. For example, when 4,4'-bipyridine is employed, each separate pyridine ring may bind to metal atoms in adjacent mixed oxide layers. The resulting composition would have individual layers within the overall $L_x$MOM'$O_4$ crystal structures bound together by bridging 4,4'-bipyridine molecules.

An X-ray powder pattern analysis of the layered reaction products demonstrates that the interlayer distance has increased in a manner correlating with the incorporation of specific Lewis bases between the layers. Thermogravimetric analysis indicates the loss of Lewis base corresponding to an approximate composition wherein x in $L_x$MOM'$O_4$ ranges from about 0.1 to 1. The fact that temperatures substantially in excess of the boiling point of the Lewis base are required to remove the Lewis base provides evidence of the covalent bonding present in the instant layered compounds.

The compounds of the invention possess unique properties and have a 2-dimensionally bonded layered structure. They are semi-conductors or insulators, are transparent to electromagnetic radiation, and are useful in electrochromic devices and as battery cathodes.

The following examples are further illustrative of the invention.

EXAMPLE 1

VOPO$_4$.2H$_2$O was refluxed in pyridine for 4 days. After this time the excess pyridine was replaced with fresh pyridine and reflux continued for a further 6 days. The final yellow product was separated by filtration and an x-ray powder pattern recorded. The lines in the x-ray pattern could all be indexed on a tetragonal unit cell (a=6.21 and c=9.62 Å). No reflections due to starting VOPO$_4$.2H$_2$O were observed. Thermogravimetric analysis of the compound in oxygen to VOPO$_4$ at 600° C. gave an overall weight loss of 32.2% compared to a theoretical weight loss of 32.8% for a stoichiometric 1:1 pyridine:VOPO$_4$ composition. The infrared spectrum of the compound showed strong absorptions at 1446, 1489 and 1604 cm$^{-1}$ characteristic of coordinated pyridine. Electron spin resonance indicated 2.5 mole % of V(IV).

EXAMPLE 2

Anhydrous VOPO$_4$ was heated with excess pyridine in a sealed pyrex ampoule for 4 days at 170° C. The yellow product was separated by filtration and analyzed by x-ray diffraction and thermogravimetric analysis. Thermogravimetric analysis in oxygen gave an overall weight loss of 29.4% compared with the theoretical of 32.8% for the 1:1 stoichiometry. An x-ray powder pattern could be completely indexed on the same tetragonal cell as in Example 1 but with slightly different lattice parameters (a=6.20, c=9.51 Å). Electron spin resonance indicated 1.5 mole % of V(IV) in the final product. The infrared spectrum is similar to that obtained in Example 1 and shows strong absorptions at 1444, 1487 and 1602 cm$^{-1}$.

EXAMPLE 3

VOPO$_4$.2H$_2$O, excess pyridine and activated molecular sieves were heated at 150° C. for 4 days in a sealed pyrex ampoule. The green product was separated from excess pyridine and the molecular sieves and characterized as described above. By thermogravimetric analysis the overall weight change of 32.7% is close to that for a stoichiometric pyridine VOPO$_4$ complex. The compound prepared by this technique, however, differs in color and in the extent of vanadium reduction indicated by the electron spin resonance (18 mole %). Moreover, the thermogravimetric analysis indicates that the major pyridine loss occurs at about 450° C. compared to about 300° C. for the compounds of Examples 1 and 2. The infrared spectrum is also characteristically different in showing a strong absorption at 1570 cm$^{-1}$.

EXAMPLE 4

Hydrated vanadyl sulfate was dried at 160° C. for 20 h to give VOSO$_4$.XH$_2$O. Anhydrous VOSO$_4$ was obtained by further dehydrating VOSO$_4$.H$_2$O at 260° C. in helium for 4 h and 350° C for ½ h. The anhydrous VOSO$_4$ was subsequently handled in a dry box to prevent rehydration. Anhydrous VOSO$_4$ and excess dry pyridine were heated in a sealed pyrex tube for 7d at 110° C. The X-ray powder pattern of the product gave a line at d=8.98 Å characteristic of the formation of a pyridine compound. A small amount of unreacted VOSO$_4$ was also observed. Analysis by thermogravimetric oxidation to V$_2$O$_5$ gave a pyridine:VOSO$_4$ ratio of 0.94:1.

EXAMPLE 5

Hydrated vanadium phosphate VOPO$_4$.2H$_2$O was heated with a solution of 4,4'-bipyridine in toluene in the presence of molecular sieves in a sealed pyrex tube for 1 day at 140° C. and then 6.5 days at 170° C. X-ray diffraction of the product showed a well developed 001 series of reflections corresponding to a layer separation of 13.0 Å. The layer separation is increased relative to that observed for the pyridine compound in Example 1 due to the larger size of the 4,4'-bipyridine molecule. Thermogravimetric oxidation to VOPO$_4$ indicated a composition close to 0.5 4,4'-bipyridine per VOPO$_4$. Some unreacted VOPO$_4$ was, however, observed in the x-ray pattern.

EXAMPLE 6

Anhydrous VOPO$_4$ was heated with a solution of 4-phenylpyridine in xylene in a sealed pyrex tube for 4 days at 150° C. After this period, the sample was removed, reground and resealed. The reaction was continued for a further eight days at 200° C. X-ray diffraction of the product revealed a series of 001 reflections corresponding to a layer separation of 14.3 Å. The layer separation is increased relative to that observed for the pyridine compound in Example 1 due to the larger size of the 4-phenylpyridine. Thermogravimetric oxidation to VOPO$_4$ indicated an overall composition of 0.42 4-phenylpyridine per VOPO$_4$. Some unreacted VOPO$_4$, however, was observed in the x-ray pattern.

EXAMPLE 7

VOAsO$_4$.2H$_2$O was synthesized by a modification of the procedure described N. G. Chernorukov et al. in the Russian Journal of Inorganic Chemistry, 23, 1479, 1978. V$_2$O$_5$ (3 g) and H$_3$AsO$_4$.½ H$_2$O were refluxed in 75 ml of water for 3 days. The resulting yellow brown solution was filtered while hot and then reduced to one quarter of its original volume. Yellow VOAsO$_4$.2H$_2$O separated and was removed by filtration, washed and dried. Anhydrous VOAsO$_4$ was prepared from the hydrated compound by heating at 200° C. in flowing helium for two hours. The anhydrous VOAsO$_4$ was subsequently handled in a dry box to prevent rehydration.

Anhydrous VOAsO$_4$ was heated with excess dry pyridine at 150° C. in a sealed pyrex tube for 10 days. The x-ray powder pattern could be indexed on a tetragonal unit cell with a=6.41 Å and c=9.70 Å together with lines due to a small amount of unreacted VOAsO$_4$. Thermogravimetric analysis of the compound in oxygen to VOAsO$_4$ gave a weight loss of 26.9% compared with the theoretical weight loss of 27.8% for the stoichiometric 1:1 pyridine:VOAsO$_4$ composition. The infrared spectrum showed strong absorptions at 1446, 1485 and 1602 cm$^{-1}$ characteristic of coordinated pyridine.

What we claim is:

1. A composition of matter comprising the reaction product of a mixed oxide having layers of corner linked octahedra and tetrahedra and a nitrogen donor Lewis base, said reaction product forming a layered compound of the formula

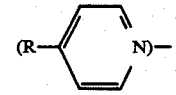

where MOM'O$_4$ is a mixed oxide selected from the group consisting of VOPO$_4$, VOSO$_4$, VOAsO$_4$, VOMoO$_4$, NbOPO$_4$, NbOAsO$_4$, TaOPO$_4$ and MoOPO$_4$, and R is hydrogen; halogen; C$_1$-C$_{20}$ aliphatic hydrocarbon, C$_6$-C$_{10}$ aryl; C$_7$-C$_{20}$ aralkyl; OR' or SR' where R' is C$_1$-C$_6$ alkyl, the layered compound being characterized in that

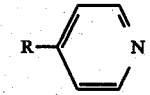

is covalently bound to a metal atom in the MOM'O$_4$ layer.

2. A composition of matter comprising the reaction product of a mixed oxide having layers of corner linked octahedra and tetrahedra and a nitrogen donor Lewis base, said reaction product forming a layered compound of the formula LMOM'O$_4$ where MOM'O$_4$ is a mixed oxide selected from the group consisting of VOPO$_4$, VOSO$_4$, VOAsO$_4$, VOMoO$_4$, NbOPO$_4$, NbOAsO$_4$, TaOPO$_4$ and MoOPO$_4$, and L is pyridine, pyridazine, pyrimidine, pyrazine and triazine, the layered compound being characterized in that L is covalently bound to a metal atom in the MOM'O$_4$ layer.

3. A composition of matter comprising the reaction product of a mixed oxide having layers of corner linked octahedra and tetrahedra and a nitrogen donor Lewis base, said reaction product forming a layered compound of the formula

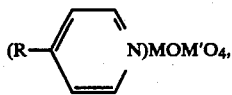

where R is hydrogen; halogen; $C_1$–$C_{10}$ aliphatic hydrocarbon, phenyl which may be substituted by halogen or $C_1$–$C_6$ alkyl; benzyl or phenylethyl; or OR′ or SR′ where R′ is $C_1$–$C_6$ alkyl, and MOM′$O_4$ is VOPO$_4$, VOMoO$_4$, VOSO$_4$ or VOAsO$_4$, the layered compound being characterized in that

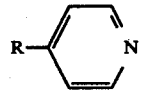

is covalently bound to a metal atom in the MOM′$O_4$ layer.

4. The composition of claim 3 wherein R is hydrogen.
5. The composition of claim 1 wherein R is hydrogen.
6. The composition of claim 1 wherein MOM′$O_4$ is VOPO$_4$.
7. The composition of claim 1 wherein MOM′$O_4$ is VOSO$_4$.
8. The composition of claim 1 wherein MOM′$O_4$ is VOAsO$_4$.
9. The composition of claim 1 wherein MOM′$O_4$ is VOMoO$_4$.

* * * * *